US008546560B2

(12) United States Patent
Kilambi

(10) Patent No.: US 8,546,560 B2
(45) Date of Patent: *Oct. 1, 2013

(54) SOLVO-THERMAL HYDROLYSIS OF CELLULOSE

(75) Inventor: Srinivas Kilambi, Marietta, GA (US)

(73) Assignee: Renmatix, Inc., King of Prussia, PA (US)

( * ) Notice: Subject to any disclaimer, the term of this patent is extended or adjusted under 35 U.S.C. 154(b) by 270 days.

This patent is subject to a terminal disclaimer.

(21) Appl. No.: 12/504,613

(22) Filed: Jul. 16, 2009

(65) Prior Publication Data

US 2010/0048884 A1 Feb. 25, 2010

Related U.S. Application Data

(60) Provisional application No. 61/081,337, filed on Jul. 16, 2008, provisional application No. 61/081,341, filed on Jul. 16, 2008, provisional application No. 61/081,348, filed on Jul. 16, 2008, provisional application No. 61/092,680, filed on Aug. 28, 2008, provisional application No. 61/224,809, filed on Jul. 10, 2009.

(51) Int. Cl.
*C07H 1/06* (2006.01)
*C07H 1/08* (2006.01)

(52) U.S. Cl.
USPC ............................. 536/127; 536/124; 536/128

(58) Field of Classification Search
None
See application file for complete search history.

(56) References Cited

U.S. PATENT DOCUMENTS

| | | |
|---|---|---|
| 1,938,802 A | 12/1933 | Braun et al. |
| 2,156,159 A | 4/1939 | Olson et al. |
| 2,198,785 A | 4/1940 | Mohr et al. |
| 2,356,500 A | 8/1944 | Boinot |
| 2,516,833 A | 8/1950 | Ant-Wuorinen |
| 2,681,871 A | 6/1954 | Wallace |
| 2,759,856 A | 8/1956 | Saums et al. |
| 2,801,939 A | 8/1957 | Hignett et al. |
| 2,810,394 A | 10/1957 | Ferguson |
| 2,822,784 A | 2/1958 | Heller et al. |
| 2,851,382 A | 9/1958 | Schmidt |
| 2,881,783 A | 4/1959 | Andrews |
| 2,994,633 A | 8/1961 | Clark |
| 2,997,466 A | 8/1961 | Ball et al. |
| 3,212,932 A | 10/1965 | Hess et al. |
| 3,314,797 A | 4/1967 | Hess et al. |
| 3,792,719 A | 2/1974 | Dickinson |
| 3,990,904 A | 11/1976 | Friese et al. |
| 4,100,016 A | 7/1978 | Diebold et al. |
| 4,105,467 A | 8/1978 | Buckl et al. |
| 4,201,596 A | 5/1980 | Church et al. |
| 4,308,200 A | 12/1981 | Fremont |
| 4,316,747 A | 2/1982 | Rugg et al. |
| 4,316,748 A | 2/1982 | Rugg et al. |
| 4,318,748 A | 3/1982 | Church |
| 4,338,199 A | 7/1982 | Modell |
| 4,363,671 A | 12/1982 | Rugg et al. |
| 4,366,322 A | 12/1982 | Raymond |
| 4,368,079 A | 1/1983 | Rugg et al. |
| 4,405,377 A | 9/1983 | Neuzil |
| 4,409,032 A | 10/1983 | Paszner et al. |
| 4,427,453 A | 1/1984 | Reitter |
| 4,468,256 A | 8/1984 | Hinger |
| 4,470,851 A | 9/1984 | Paszner et al. |
| 4,493,797 A | 1/1985 | Avedesian |
| 4,520,105 A | 5/1985 | Sinner et al. |
| 4,535,593 A | 8/1985 | Sakka |
| 4,543,190 A | 9/1985 | Modell |
| 4,556,430 A | 12/1985 | Converse et al. |
| 4,607,819 A | 8/1986 | Spils |
| 4,612,286 A | 9/1986 | Sherman et al. |
| 4,637,835 A | 1/1987 | Nagle |
| 4,644,060 A | 2/1987 | Chou |
| 4,645,541 A | 2/1987 | DeLong |
| 4,674,285 A | 6/1987 | Durrant et al. |
| 4,675,198 A | 6/1987 | Sevenants |
| 4,699,124 A | 10/1987 | Nagle |
| 4,742,814 A | 5/1988 | Sinner et al. |
| 4,764,596 A | 8/1988 | Lora et al. |
| 4,857,638 A | 8/1989 | Yalpani et al. |
| 4,946,946 A | 8/1990 | Fields et al. |
| 4,964,995 A | 10/1990 | Chum et al. |
| 5,009,746 A | 4/1991 | Hossain et al. |
| 5,041,192 A | 8/1991 | Sunol et al. |
| 5,125,977 A | 6/1992 | Grohmann et al. |
| 5,169,687 A | 12/1992 | Sunol |
| 5,196,460 A | 3/1993 | Lora et al. |
| 5,213,660 A | 5/1993 | Hossain et al. |
| 5,328,934 A | 7/1994 | Schiraldi |
| 5,338,366 A | 8/1994 | Grace et al. |
| 5,411,594 A | 5/1995 | Brelsford |
| 5,424,417 A | 6/1995 | Torget et al. |
| 5,503,996 A | 4/1996 | Torget et al. |
| 5,512,231 A | 4/1996 | Thies et al. |
| 5,516,952 A | 5/1996 | Lee et al. |
| 5,536,325 A | 7/1996 | Brink |

(Continued)

FOREIGN PATENT DOCUMENTS

| | | |
|---|---|---|
| AU | 2002234469 | 7/2007 |
| CA | 1010859 | 5/1977 |

(Continued)

OTHER PUBLICATIONS

Schacht et al. J. of Supercritical Fluids (2008), vol. 46, pp. 299-321.*

(Continued)

*Primary Examiner* — Patrick Lewis
(74) *Attorney, Agent, or Firm* — Kilpatrick Townsend & Stockton LLP; Travis B. Gasa

(57) ABSTRACT

The invention relates to a process for hydrolyzing cellulose, comprising: (a) contacting cellulose with a fluid mixture comprising supercritical $CO_2$ and sub-critical or near-critical water to form a reactant mixture at a first temperature and first pressure for a first time period, wherein a reaction occurs and forms one or more hydrolysis products; (b) quenching the reaction; and (c) recovering at least one hydrolysis product.

15 Claims, 4 Drawing Sheets

(56) References Cited

U.S. PATENT DOCUMENTS

| | | |
|---|---|---|
| 5,558,783 A | 9/1996 | McGuinness |
| 5,628,830 A | 5/1997 | Brink |
| 5,705,369 A | 1/1998 | Torget et al. |
| 5,788,812 A | 8/1998 | Agar et al. |
| 5,811,527 A | 9/1998 | Ishitoku et al. |
| 5,824,187 A | 10/1998 | Richter et al. |
| 5,830,763 A | 11/1998 | Junk et al. |
| 5,980,640 A | 11/1999 | Nurmi et al. |
| 6,022,419 A | 2/2000 | Torget et al. |
| 6,025,452 A | 2/2000 | Kurple |
| 6,090,291 A | 7/2000 | Akai et al. |
| 6,180,845 B1 | 1/2001 | Catallo et al. |
| 6,228,177 B1 | 5/2001 | Torget |
| 6,419,788 B1 | 7/2002 | Wingerson |
| 6,555,350 B2 | 4/2003 | Ahring et al. |
| 6,569,640 B1 | 5/2003 | Castor et al. |
| 6,642,396 B1 | 11/2003 | Zeitsch et al. |
| 6,743,928 B1 | 6/2004 | Zeitsch |
| 6,872,316 B2 | 3/2005 | Heikkilä et al. |
| 6,878,212 B1 | 4/2005 | Pinatti et al. |
| 6,921,820 B2 | 7/2005 | Arai et al. |
| 6,929,752 B2 | 8/2005 | Cansell |
| 7,189,306 B2 | 3/2007 | Gervais |
| 7,238,242 B2 | 7/2007 | Pinatti et al. |
| 7,259,231 B2 | 8/2007 | Cornish et al. |
| 7,262,331 B2 | 8/2007 | van de Beld et al. |
| 7,476,296 B2 | 1/2009 | Appel et al. |
| 7,547,539 B2 | 6/2009 | Ikegami et al. |
| 7,566,383 B2 | 7/2009 | Everett et al. |
| 7,585,652 B2 | 9/2009 | Foody et al. |
| 7,649,086 B2 | 1/2010 | Belanger et al. |
| 7,666,637 B2 | 2/2010 | Nguyen |
| 7,670,813 B2 | 3/2010 | Foody et al. |
| 7,754,457 B2 | 7/2010 | Foody et al. |
| 7,771,699 B2 | 8/2010 | Adams et al. |
| 7,955,508 B2 | 6/2011 | Allan et al. |
| 7,960,325 B2 | 6/2011 | Kluko |
| 8,030,039 B1 | 10/2011 | Retsina et al. |
| 8,057,639 B2 | 11/2011 | Pschorn et al. |
| 8,282,738 B2 | 10/2012 | Kilambi et al. |
| 2001/0050096 A1 | 12/2001 | Costantini et al. |
| 2002/0061583 A1 | 5/2002 | Kawamura et al. |
| 2002/0069987 A1 | 6/2002 | Pye |
| 2003/0156970 A1 | 8/2003 | Oberkofler et al. |
| 2003/0221361 A1 | 12/2003 | Russell et al. |
| 2004/0020854 A1 | 2/2004 | Ali et al. |
| 2004/0231661 A1 | 11/2004 | Griffin et al. |
| 2005/0065336 A1 | 3/2005 | Karstens |
| 2006/0281913 A1 | 12/2006 | Ferreira et al. |
| 2007/0108036 A1 | 5/2007 | Siskin et al. |
| 2007/0148751 A1 | 6/2007 | Griffin et al. |
| 2007/0161095 A1 | 7/2007 | Gurin |
| 2007/0217980 A1 | 9/2007 | Garcia-Ortiz et al. |
| 2007/0254348 A1 | 11/2007 | Retsina et al. |
| 2007/0259412 A1 | 11/2007 | Belanger et al. |
| 2007/0267008 A1 | 11/2007 | Funazukuri et al. |
| 2008/0015336 A1 | 1/2008 | Cornish et al. |
| 2008/0032344 A1 | 2/2008 | Fallavollita |
| 2008/0051566 A1 | 2/2008 | Ohman et al. |
| 2008/0292766 A1 | 11/2008 | Hoffman et al. |
| 2008/0295981 A1 | 12/2008 | Shin et al. |
| 2008/0302492 A1 | 12/2008 | Shin et al. |
| 2009/0023187 A1 | 1/2009 | Foody et al. |
| 2009/0038212 A1 | 2/2009 | Cooper |
| 2009/0056201 A1 | 3/2009 | Morgan |
| 2009/0118477 A1 | 5/2009 | Hallberg et al. |
| 2009/0176286 A1 | 7/2009 | O'Connor et al. |
| 2009/0176979 A1 | 7/2009 | Hara et al. |
| 2009/0205546 A1 | 8/2009 | Kluko |
| 2009/0221814 A1 | 9/2009 | Pschorn et al. |
| 2009/0223612 A1 | 9/2009 | McKnight et al. |
| 2009/0229599 A1 | 9/2009 | Zhang |
| 2009/0232892 A1 | 9/2009 | Yamasaki et al. |
| 2009/0288788 A1 | 11/2009 | Castor |
| 2010/0004119 A1 | 1/2010 | Gadkaree et al. |
| 2010/0012583 A1 | 1/2010 | Stuart |
| 2010/0043782 A1 | 2/2010 | Kilambi |
| 2010/0048924 A1 | 2/2010 | Kilambi |
| 2010/0055629 A1 | 3/2010 | McKnight et al. |
| 2010/0063271 A1 | 3/2010 | Allan et al. |
| 2010/0069626 A1 | 3/2010 | Kilambi |
| 2010/0077752 A1 | 4/2010 | Papile |
| 2010/0081798 A1 | 4/2010 | Balensiefer et al. |
| 2010/0136634 A1 | 6/2010 | Kratochvil et al. |
| 2010/0136642 A1 | 6/2010 | Belanger et al. |
| 2010/0146842 A1 | 6/2010 | Dumenil |
| 2010/0146843 A1 | 6/2010 | Dumenil |
| 2010/0152509 A1 | 6/2010 | Ekman |
| 2010/0159569 A1 | 6/2010 | Medoff et al. |
| 2010/0175690 A1 | 7/2010 | Nagahama et al. |
| 2010/0184151 A1 | 7/2010 | Tolan et al. |
| 2010/0233771 A1 | 9/2010 | McDonald et al. |
| 2010/0269990 A1 | 10/2010 | Dottori et al. |
| 2010/0279361 A1 | 11/2010 | South et al. |
| 2010/0326610 A1 | 12/2010 | Harvey et al. |
| 2010/0329938 A1 | 12/2010 | Allan et al. |
| 2010/0330638 A1 | 12/2010 | Aita et al. |
| 2011/0021743 A1 | 1/2011 | Cornish et al. |
| 2011/0076724 A1 | 3/2011 | Dumenil |
| 2011/0079219 A1 | 4/2011 | McDonald et al. |
| 2011/0100359 A1 | 5/2011 | North |
| 2011/0126448 A1 | 6/2011 | Dumenil |
| 2011/0137085 A1 | 6/2011 | Trahanovsky et al. |
| 2011/0151516 A1 | 6/2011 | Van Der Heide et al. |
| 2011/0165643 A1 | 7/2011 | Retsina et al. |
| 2011/0171709 A1 | 7/2011 | Bardsley |
| 2011/0192560 A1 | 8/2011 | Heikkila et al. |
| 2011/0232160 A1 | 9/2011 | Siskin et al. |
| 2011/0237838 A1 | 9/2011 | Zmierczak et al. |
| 2011/0239973 A1 | 10/2011 | Qin |
| 2011/0253326 A1 | 10/2011 | Sherman et al. |
| 2011/0287502 A1 | 11/2011 | Castor |
| 2011/0294991 A1 | 12/2011 | Lake et al. |
| 2012/0103325 A1 | 5/2012 | Koenig et al. |
| 2012/0108798 A1 | 5/2012 | Wenger et al. |
| 2012/0116063 A1 | 5/2012 | Jansen et al. |
| 2012/0145094 A1 | 6/2012 | Simard |
| 2012/0146784 A1 | 6/2012 | Hines et al. |
| 2012/0184788 A1 | 7/2012 | Loop et al. |

FOREIGN PATENT DOCUMENTS

| | | |
|---|---|---|
| CA | 1284637 | 6/1991 |
| CN | 1680415 | 10/2005 |
| CN | 1931866 | 3/2007 |
| CN | 101200479 | 6/2008 |
| CN | 101613970 | 12/2009 |
| CN | 101736631 | 6/2010 |
| CN | 101787398 | 7/2010 |
| CN | 101886143 | 11/2010 |
| CZ | 225851 | 3/1984 |
| CZ | 248106 | 1/1987 |
| DE | 3225074 | 1/1984 |
| DE | 10259928 A1 | 7/2004 |
| EP | 0037912 | 10/1981 |
| EP | 1194226 | 9/2004 |
| EP | 1364072 | 1/2007 |
| EP | 1527204 | 4/2008 |
| EP | 1836181 | 3/2009 |
| FR | 2580669 | 10/1986 |
| GB | 291991 | 6/1928 |
| GB | 692284 | 6/1953 |
| GB | 1245486 | 9/1971 |
| GB | 1569138 | 6/1980 |
| GB | 2145090 | 3/1985 |
| JP | 50145537 | 11/1975 |
| JP | 56045754 | 4/1981 |
| JP | 57061083 | 4/1982 |
| JP | 62283988 | 12/1987 |
| JP | 04197192 | 7/1992 |
| JP | 11226385 | 8/1999 |
| JP | 2001095594 | 4/2001 |
| JP | 2001262162 | 9/2001 |
| JP | 2003212888 | 7/2003 |
| JP | 2005040025 | 2/2005 |

| | | |
|---|---|---|
| JP | 2005296906 | 10/2005 |
| JP | 2006223152 | 8/2006 |
| JP | 2006263527 | 10/2006 |
| JP | 2007313476 | 12/2007 |
| JP | 2008011753 | 1/2008 |
| JP | 2008035853 | 2/2008 |
| JP | 2008292018 | 12/2008 |
| JP | 2009189291 | 8/2009 |
| JP | 201132388 | 2/2011 |
| KR | 2009030967 | 3/2009 |
| KR | 20090039470 | 4/2009 |
| KR | 20100032242 | 3/2010 |
| RU | 2371002 | 10/2009 |
| WO | 8300370 | 2/1983 |
| WO | 8301958 | 6/1983 |
| WO | 9817727 | 4/1998 |
| WO | 9923260 | 5/1999 |
| WO | 9967409 | 12/1999 |
| WO | 0061276 | 10/2000 |
| WO | 0160752 | 8/2001 |
| WO | 0204524 | 1/2002 |
| WO | 02070753 | 9/2002 |
| WO | WO-2007056701 | 5/2007 |
| WO | 2008026932 | 3/2008 |
| WO | 2008036500 | 3/2008 |
| WO | 2008050740 | 5/2008 |
| WO | 2008121043 | 10/2008 |
| WO | 2008143078 | 11/2008 |
| WO | WO-2009015409 | 2/2009 |
| WO | 2009108773 | 9/2009 |
| WO | WO-2010009343 | 1/2010 |
| WO | 2010034055 | 4/2010 |
| WO | 2010045576 | 4/2010 |
| WO | 2010046532 | 4/2010 |
| WO | 2010069516 | 6/2010 |
| WO | 2010113129 | 10/2010 |
| WO | 2010121367 | 10/2010 |
| WO | 2011002822 | 1/2011 |
| WO | 2011091044 | 7/2011 |
| WO | WO-2011091044 | 7/2011 |
| WO | 2011094859 | 8/2011 |

OTHER PUBLICATIONS

Pasquini et al. J. of Supercritical Fluids (2005), vol. 36, pp. 31-39.*
Pasquini et al. J. of Supercritical Fluids (2005), vol. 34, pp. 125-134.*
Moreschi et al. J. Agric. Food Chem. (2004), vol. 52, pp. 1753-1758.*
Merriam-Webster Dictionary, "Quench-Defintion", viewed Jan. 25, 2012. <http://www.merriam-webster.com/dictionary/quench>.*
Kamm et al. Appl. Microbiol. Biotechnol. (2004), vol. 64, pp. 137-145.*
Hamelinck et al. Biomass and Bioenergy (2005), vol. 28, pp. 384-410.*
PCT Application No. PCT/US2009/050898, International Preliminary Report on Patentability mailed Jan. 18, 2011.
PCT Application No. PCT/US2009/050898, International Search Report and Written Opinion mailed Feb. 8, 2010.
Adschiri, et al., "Noncatalytic Conversion of Cellulose in Supercritical and Sub-Critical Critical Water", Journal of Chemical Engineering of Japan, 1993, 26(6):676-680.
Bennett, et al., "Chemicals from Forest Products by Supercritical Fluid Extraction", Fluid Phase Equil., 1983, 10:337.
Bicker, et al., "Catalytical conversion of carbohydrates in subcritical water: A new chemical process for lactic acid production", Journal of Molecular Catalysis A: Chemical 239, 2005, 151-157.
Boocock, et al., "Liquefaction of Biomass by Rapid Hydrolysis", Can. J. Chem. Eng., 1983, 61:80.
Chamblee, et al., "Reversible in situ acid formation for β-pinene hydrolysis using $CO_2$ expanded liquid and hot water", Green Chemistry, 2004, vol. 6, 382-386.
Dias, et al. "Dehydration of xylose into fufural over micro-mesoporous sulfonic acid catalysts", Journal of Catalysis 229, 2005, 414-423.
Eckert, et al., "Environmental Science and Technology", 1986, 20:319-325.
Ehara, et al. "A comparative study on chemical conversion of cellulose between the batch-type and flow-type in supercritical water", Cellulose, 2002, 9:301-311.

Erzengin, et al., "Liquefaction of Sunflower Stalk by Using Supercritical Extraction", Energy Conversion and Management, Elsevier Science Publishers, Oxford, GB Aug. 1998, 39:11, 1203-1206.
Guirong, et al., "Cellulose decomposition behavior in hot-compressed aprotic solvents", Science in China Series B: Chemistry, May 2008, vol. 51, No. 5, 479-486.
Houghton, et al., "Reactivity of Some Organic Compounds with Supercritical Water", Fuel 1986, 61:827.
Kim, et al., "Selective Synthesis of Furfural from Xylose with Supercritical Carbon Dioxide and Solid Acid Catalyst", Journal of Industrial and Engineering Chemistry, The Korean Society of Industrial and Engineering Chemistry, Korea 2001, 7(6); 424-429.
Knopf, et al., "Reactive Extraction of Lignin from Biomass Using Supercritical Ammonia-Water Mixtures", J. Supercritical Fluids 1993, 6:249-254.
Li, et al., "Interaction of Supercritical Fluids with Lignocellulosic Materials", Industrial and Engineering Chemistry Research 1988, 27(7): 1301-1312.
Marchessault, et al., "A New Understanding of the Carbohydrate System", Future Sources of Organic Raw Materials 1980, 613-625.
Matsumura, et al. "Supercritical Water Treatment of Biomass for Energy and Material Recovery", Combust. Sci. and Tech., 2006, 178: 509-536.
McCoy, et al., "Extraction of Lignin from Biomass with Supercritical Alcohol", J. Supercritical Fluids 1989, 2:80-84.
McHugh, et al., "Supercritical Fluid Extraction : Principles and Practice", Butterworths 1986, 309-310.
Miyazawa, et al., "Polysaccharide Hydrolysis Accelerated by Adding Carbon Dioxide under Hydrothermal Conditions", Biotechnol. Prog. 2005, 21:1782-1785.
Modell, et al., "Supercritical Water Oxidation of Pulp Mill Sludges", TAPPI J. 1992, 75:195.
Ogihara, et al. "Direct observation of cellulose dissolution in subcritical and supercritical water over a wide range of water densities (500-1000 $kg/m^3$)", Cellulose, 2005, 12:595-606.
Osada, et al., "Low Temperature Catalytic Gasification of Lignin and Cellulose with a Ruthenium Catalyst in Supercritical Water", Energy Fuels 2004, 18: 327-333.
Pasquini, et al., "Extraction of Lignin from sugar cane bagasse and Pinus taeda wood chips using ethanol-water mixtures and carbon dioxide at high pressures", Journal of Supercritical Fluids, PRA Press, US Nov. 2005, 36(1); 31-39.
Persson, et al., "Supercritical Fluid Extraction of a Lignocellulosic Hydrolysate of Spruce for Detoxification and to Facilitate Analysis of Inhibitors", Biotechnology and Bioengineering, Wiley & Sons , Hoboken, NJ, US Sep. 20, 2002, 79(6):694-700.
Peter, et al., "High Pressure Extraction of Lignin from Biomass", Supercritical Fluid Technology, p. 385 (1985).
Rao, et al., "Pyrolysis Rates of Biomass Materials", Energy 1998, 23:973-978.
Sako, "Kinetic study of furfural formation accompanying supercritical carbon dioxide extraction", Journal of Chemical Engineering of Japan, Society of Chemical Engineers Aug. 1, 1992, 25(4):372-377.
Sangarunlert, et al., "Furfural production by acid hydrolysis and supercritical carbon dioxide extraction from rice husk", Korean Journal of Chemical Engineering 2007, 24(6): 936-941.
Sasaki, et al., "Cellulose Hydrolysis in Sub-Critical and Supercritical Water", Journal of Supercritical Fluids 1998, 13:261-268.
Sina, et al. "Key Compounds of the Hydropyrolysis of Glucose in Supercritical Water in the Presence of $K_2CO_3$", Ind. Eng. Chem. Res., 2003, 42(15), 3516-3521.
Walsum, et al. "Carbonic acid enhancement of hydrolysis in aqueous pretreatment of corn stover", Bioresource Technology 93, 2004, 271-226.
Yoshida, et al., "Gasification of Biomass Model Compound and Real Biomass in Supercritical Water", Biomass and Bioenergy, 26:71-78 (2004).
International PCT Application No. PCT/US2011/21726, International Search Report and Written Opinion dated Jul. 5, 2011.
Holgate, et al., "Glucose Hydrolysis and Oxidation in Supercritical Water", AIChE Journal, 1995, 41(3), 637-636.

Li, et al., "Interaction of Supercritical Fluids with Lignocellulosic Materials", Industrial Engineering Chemistry Research, American Chemical Society Res., Jul. 1988, 27(7):1301-1312.

Lu, et al., "Decomposition of Cellulose to Produce 5-hydroxymethylfuraldehyde in Subcritical Water", Abstract of Transactions of Tranjin University, STN Accession No. 2008:1016799, Document No. 151:427986, 2008, 14(3), 198-201.

Moreschi, et al., "Hydrolysis of Ginger Bagasse Starch in Subcritical Water and Carbon Dioxide", Journal of Agricultural and Food Chemistry, 2004, 52(6), 1753-1758.

Saito, et al., "The Investigation of Degradation Reaction of Various Saccharides in High Temperature and High Pressure Water", Journal of Physics:Conference Series, 2008, 121.

Wiboonsiriku, et al., "Properties of Extracts from Defatted Rice Bran by its Subcritical Water Treatment", Journal of Agricultural and Food Chemistry, 2007, 55(21), 8759-8765.

Zhao, et al., "Supercritical hydrolysis of cellulose for oligosaccharide production in combined technology", Chemical Engineering Journal, Aug. 1, 2009, 150(2):411-417.

U.S. Appl. No. 12/504,613, Non-Final Office Action mailed Sep. 26, 2011.

U.S. Appl. No. 12/504,628, Non-Final Office Action mailed Aug. 8, 2011.

U.S. Appl. No. 12/504,628, Notice of Allowance mailed Dec. 7, 2011.

U.S. Appl. No. 12/504,628, Response to Office Action filed Oct. 27, 2011.

U.S. Appl. No. 12/504,628, Supplemental Response filed Nov. 14, 2011.

U.S. Appl. No. 12/504,636, Office Action mailed Nov. 10, 2011.

U.S. Appl. No. 12/504,611, "Response to Final Office Action", filed May 30, 2012 (22 pages).

U.S. Appl. No. 12/504,636, "Response to Office Action", filed Jun. 8, 2012 (10 pages).

U.S. Appl. No. 12/504,636, Office Action mailed Apr. 23, 2012 (11 pages).

European Patent Application No. 09790548.3, Article 94(3) EPC, mailed Mar. 30, 2012 (8 pages).

(Abstract) "Evaluation of materials for use in letdown valves and coal feed pumps for coal liquefaction service", Electr Power Res Inst Rep EPRIAF, No. 579, 1978, 94.

(Abstract) "Evaluation of materials for use in letdown valves for coal liquefaction service", Annual Conference on Materials for Coal Conversion and Utilization (CONF-791014), Oct. 9-11, 1979.

U.S. Appl. No. 12/504,611, "Office Action" mailed Aug. 2, 2012 (32 pages).

U.S. Appl. No. 12/504,636, "Notice of Allowance" mailed Jul. 27, 2012 (11 pages).

Adschiri et al., "Noncatalytic Conversion of Cellulose in Supercritical and Sub-Critical Water", Journal of Chemical Engineering of Japan, 1993, 26(6): 676-680.

Adschiri et al., "Cellulose hydrolysis in supercritical water to recover chemicals", Reaction Engineering for Pollution Prevention, 2000, 205-220.

Arai et al., "(Abstract) Biomass conversion in supercritical water for chemical recycle", Enerugi, Shigen, 16(2), 1995, 175-180.

Baek et al., "(Abstract) Optimization of the pretreatment of rice straw hemicellulose hydrolyzates for microbial production of xylitol", Biotechnology and Bioprocess Engineering, 12(4), 2007, 404-409.

Balhouse, "(Abstract) Design, fabrication, and evaluation of a spiral-flow letdown valve", Electric Power Research Institute, Advanced Power Systems Division, EPRI AP, 1981.

Ballesteros et al., "(Abstract) Fractionation of *Cynara cardunculus* (cardoon) biomass by dilute-acid pretreatment", Applied Biochemistry and Biotechnology, 137-140, 2007, 239-252.

Bobleter , "Hydrothermal Degradation and Fractionation of Saccharides and Polysaccharides", 1998.

Bustos et al., "(Abstract) Modeling of the hydrolysis of sugar cane bagasse with hydrochloric acid", Applied Biochemistry and Biotechnology, 104(1), 2003, 51-68.

Carrasco et al., "(Abstract) SO2-catalyzed steam pretreatment and fermentation of enzymatically hydrolyzed sugarcane bagasse", Enzyme and Microbial Technology, 46(2), 2010, 64-73.

Carrasco et al., "(Abstract) Effects of dilute acid and steam explosion pretreatments on the cellulose structure and kinetics of cellulosic fraction hydrolysis by dilute acids in lignocellulosic materials", Applied Biochemistry and Biotechnology, 45-46, 1994, 23-34.

Chen et al., "(Abstract) Study on dilute-acid pretreatment of corn stalk", Linchan Huaxue Yu Gongye, 29(2), 2009, 27-32.

Converti et al., "(Abstract) Wood hydrolysis and hydrolyzate detoxification for subsequent xylitol production", Chemical Engineering & Technology, 23(11), 2000, 1013-1020.

Do Egito De Paiva et al., "(Abstract) Optimization of D-xylose, L-arabinose and D-glucose production obtained from sugar cane bagasse hydrolysis process", Brazilian Symposium on the Chemistry of Lignins and Other Wood Components, 6th, 2001, 333-337.

Dogaris et al., "(Abstract) Hydrothermal processing and enzymatic hydrolysis of sorghum bagasse for fermentable carbohydrates production", Bioresource Technology, 100(24), 2009, 6543-6549.

Ehara et al., "Characterization of the lignin-derived products from wood as treated in supercritical water", Journal of Wood Science, vol. 48, No. 4, Aug. 2002, pp. 320-325.

Ehara et al., "Decomposition behavior of cellulose in supercritical water, subcritical water, and their combined treatments", J. Wood Sci., vol. 51, 2005, 148-153.

Ehrman , "Methods for the chemical analysis of biomass process streams", Handbook on Bioethanol, 1996, 395-415.

European Patent Application No. 09790548.3 , "Response to Article 94(3) Communication" mailed Jul. 24, 2012 (13 pages).

Garrote et al., "(Abstract) Manufacture of xylose-based fermentation media from corncobs by posthydrolysis of autohydrolysis liquors", Applied Biochemistry and Biotechnology, 95(3), 2001, 195-207.

Geddes et al., "(Abstract) Optimizing the saccharification of sugar cane bagasse using dilute phosphoric acid followed by fungal celluloses", Bioresource Technology, 101(6), 2010, 1851-1857.

Gong et al., "(Abstract) Study on hydrolysis and saccharification of microcrystalline cellulose in supercritical water", Xiandai Huagong, 30(2), 2010, 44-47.

Harmer et al., "(Abstract) A new route to high yield sugars from biomass: phosphoric-sulfuric acid", Chemical Communications, vol. 43, 2009, 6610-6612.

Herrera et al., "(Abstract) Production of Xylose from Sorghum Straw Using Hydrochloric Acid", Journal of Cereal Science, 37(3), 2003, 267-274.

Hosaka , "(Abstract) Filtration of lignin in hydrolysis solution", Hiroshima Daigaku Suichikusangakubu Kiyo, 17(1), 1978, 17-25.

Ioannidou et al., "Direct determination of toxic trace metals in honey and sugars using inductively coupled plasma atomic emission spectrometry", Talanta, 65(1), 2005, 92-97.

Jensen et al., "(Abstract) Effects of dilute acid pretreatment conditions on enzymatic hydrolysis monomer and oligomer sugar yields for aspen, balsam, and switchgrass", Bioresource Technology, 101(7), 2010, 2317-2325.

Jeong et al., "(Abstract) Optimizing dilute-acid pretreatment of rapeseed straw for extraction of hemicellulose", Applied Biochemistry and Biotechnology, 161(1-8), 2010, 22-33.

Jiang et al., "(Abstract) A method for quick analysis of biomass chemical composition from element analysis", Huagong Xuebao (Chinese Edition), 61(6), 2010, 1506-1509.

Kamada et al., "(Abstract) Development of letdown valve on pilot plant", Sekitan Kagaku Kaigi Happyo Ronbunshu, 35th, 1998, 459-462.

Karimi et al., "(Abstract) Conversion of rice straw to sugars by dilute-acid hydrolysis", Biomass and Bioenergy, 30(3), 2006, 247-253.

Kupianen et al., "(Abstract) Comparison of formic and sulfuric acids as a glucose decomposition catalyst", Ind. Eng. Chem. Res., 49(18), 2010, 8444-8449.

Lee et al., "(Abstract) Hydrolysis of cellulose under subcritical and supercritical water using continuous flow system", Hwahak Konghak, 39(2), 2001, 257-263.

Levai , "(Abstract) Atom spectrometric methods for determination of trace metal impurities in pharmaceutical substances", Acta Pharmaceutica Hungarica, 71(3), 2001, 350-356.

Li, "(Abstract) Analysis of failure cause in CCI pressure reducing valves used in product pipeline", Guandao Jishu Yu Shebei, (5), 2008, 34-36.

Li et al., "(Abstract) Studies of Monosaccharide Production through Lignocellulosic Waste Hydrolysis Using Double Acids", Energy & Fuelds, 22(3), 2008, 2015-2021.

Li et al., "(Abstract) Improvement on technology of extracting xylose from the corncobs by acid method", Shipin Gongye Keji, 30(6), 2009, 263-264.

Li et al. "Fructose decomposition kinetics in organic acides-enriched high termperature liquid water", Biomass and Bioenergy, vol. 33, Issue 9, Sep. 2009, 1182-1187.

Li et al., "(Abstract) Study on the recovery of lignin from black liquor by ultrafiltration", Huaxue Gongcheng, 31(1), 2003, 49-52.

Lloyd et al., "(Abstract) Combined sugar yields for dilute sulfuric acid pretreatment of corn stover followed by enzymatic hydrolysis of the remaining solids", Bioresource Technology, 96(18), 2005, 1967-1977.

Lopez et al., "(Abstract) Chemical characterization and dilute-acid hydrolysis of rice hulls from an artisan mill", BioResources, 5(4), 2010, 2268-2277.

Lu et al., "(Abstract) Optimization of $H_2SO_4$-catalyzed hydrothermal pretreatment of rapeseed straw for bioconversion to ethanol: focusing on pretreatment at high solids content", Bioresource Technology, 100(12), 2009, 3048-3053.

Luterbacher et al., "(Abstract) High-Solids Biphasic $CO_2$-$H_2O$ Pretreatment of Lignocellulosic Biomass", Biotechnology and Bioengineering, 107(3), 2010, 451-460.

Malaluan et al., "(Abstract) Biomass conversion in supercritical water", Off. Proc. Comb. Conf., 6th Conf. Asia Pac. Confed. Chem. Eng., 21st Australas. Chem. Eng. Conf., vol. 1 (Publisher: Inst. Eng., Aus., Barton, Australia), 1993, 209/1-214/1.

Marone et al., "(Abstract) Comminution of hydrolytic lignin in a jet mill", Gidroliznaya i Lesokhimicheskaya Promyshlennost, (6), 1991, 14-15.

Matsunaga et al., "(Abstract) Super-rapid chemical conversion of sugi wood by supercritical and subcritical water treatment", Mokuzai Gakkaishi, 50(5), 2004, 325-332.

McWilliams et al., "(Abstract) Comparison of aspen wood hydrolysates produced by pretreatment with liquid hot water and carbonic acid", Applied Biochemistry and Biotechnology, 98-100, 2002, 109-121.

Miller-Ihli et al., "Direct determination of lead in sugars using graphite furnace atomic absorption spectrometry", Atomic Spectroscopy, 14(4), 1993, 85-9.

Mok et al., "(Abstract) Dilute acid hydrolysis of biopolymers in a semi-batch flow reactor at supercritical pressure", Energy from Biomass and Wastes, 13, 1990, 1329-1347.

Mosier et al., "(Abstract) Optimization of pH controlled liquid hot water pretreatment of corn stover", Bioresource Technology, 96(18), 2005, 1986-1992.

Mosier et al., "Characterization of Acid Catalytic Domains for Cellulose Hydrolysis and Glucose Degradation", Biotechnology and Bioengineering, vol. 79, No. 6, Sep. 20, 2002, 610-618.

Nakata et al., "(Abstract) Bioethanol from cellulose with supercritical water treatment followed by enzymatic hydrolysis", Applied Biochemistry and Biotechnology, 129-132, 2006, 476-485.

Napradean et al., "(Abstract) Studies regarding cadmium determination by atomic absorption spectrometry. Note II. Pharmaceutical finished products", Farmacia, 53(2), 2005, 86-90.

Neureiter et al., "(Abstract) Dilute acid hydrolysis of presscakes from silage and grass to recover hemicellulose-derived sugars", Bioresource Technology, 92(1), 2004, 21-29.

Neureiter et al., "(Abstract) Dilute-acid hydrolysis of sugarcane bagasse at varying conditions", Applied Biochemistry and Biotechnology, 98-100, 2002, 49-58.

Nunn et al., "Product compositions and kinetics in the rapid pyrolysis of milled wood lignin", Industrial & Engineering Chemistry Process Design and Development, vol. 24, Jul. 1985, pp. 844-852.

Parajo et al., "(Abstract) Pre-hydrolysis of Eucalyptus wood with dilute sulfuric acid: operation in autoclave", Holz als Roh- und Werkstoff, 52(2), 1994, 102-8.

Park et al., "(Abstract) Kinetics of cellulose decomposition under subcritical and supercritical water in continuous flow system", Korean Journal of Chemical Engineering, 19(6), 2002, 960-966.

Pessoa, Jr. et al., "(Abstract) Acid hydrolysis of hemicellulose from sugarcane bagasse", Brazilian Journal of Chemical Engineering, 14(3), 1997, 291-297.

Pohl et al., "Direct determination of the total concentrations of magnesium, calcium, manganese, and iron in addition to their chemical and physical fractions in dark honeys", Analytical Letters, 44(13), 2011, 2265-2279.

Ramirez et al., "(Abstract) Mathematical modelling of feed pretreatment for bioethanol production", Computer-Aided Chemical Engineering, vol. 26, 2009, 1299-1304.

Roberto et al., "(Abstract) Dilute-acid hydrolysis for optimization of xylose recovery from rice straw in a semi-pilot reactor", Industrial Crops and Products, 17(3), 2003, 171-176.

Saka et al., "Chemical conversion of biomass resources to useful chemicals and fuels by supercritical water treatment", Bridgewater AV(ed) Progress in Thermocritical Biomass Conversion. Blackwell, Oxford, 2001, 1338-1348.

Saka, "(Abstract) Supercritical fluids to biomass research", Cellulose Communications, 5(3), 1998, 129-135.

Saka et al., "(Abstract) Supercritical fluids to biomass research (II)", Cellulose Communications, 9(3), 2002, 137-143.

Saka et al., "Chemical conversion of various celluloses to glucose and its derivatives in supercritical water", Cellulose Communications, 6(3), 1999, 177-191.

Sanchez et al., "(Abstract) Dilute-acid hydrolysis for fermentation of the Bolivian straw material Paja Brava", Bioresource Technology, 93(3), 2004, 249-256.

Sarrouh et al., "(Abstract) Biotechnological production of xylitol: enhancement of monosaccharide production by post-hydrolysis of dilute acid sugarcane hydrolysate", Applied Biochemistry and Biotechnology, 153(1-3), 2009, 163-170.

Sasaki et al., "Direct hydrolysis of cellulose to glucose using ultra-high temperature and pressure steam explosion", Carbohydrate Polymers 89, 2012, 298-301.

Sasaki et al., "Rapid and selective conversion of cellulose to valuable chemical intermediates using supercritical water", Proc. 6th international Symposium on Supercritical Fluids, Tome 2, 2003, 1417-1422.

Sasaki et al., "(Abstract) Super-rapid enzymatic hydrolysis of cellulose with supercritical water solubilization pretreatment", Kobunshi Ronbunshu, 58(10), 2001, 527-532.

Sasaki et al., "Dissolution and Hydrolysis of Cellulose in Subcritical and Supercritical Water", Industrial & Engineering Chemistry Research, 39(8), 2000, 2883-2890.

Sasaki et al., "Kinetics of cellulose conversion at 25 MPa in sub- and supercritical water", AIChE Journal, 50(1), 2004, 192-202.

Saucedo-Luna et al., "(Abstract) Optimization of acid hydrolysis of bagasse from *Agave tequilana* Weber", Revista Mexicana de Ingenieria Quimica, 9(1), 2010, 91-97.

Sera et al., "(Abstract) Development of saccharification techniques for cellulosic biomass", Hitz Giho, 68(2), 2008, 40-45.

Shikinaka et al., "(Abstract) Polyfunctional nanometric particles obtained from lignin, a woody biomass resource", Green Chemistry, 12(11), 2010, 1914-1916.

Soederstroem et al., "(Abstract) Effect of Washing on Yield in One- and Two-Step Steam Pretreatment of Softwood for Production of Ethanol", Biotechnology Progress, 20(3), 2004, 744-749.

Sokolov et al., "(Abstract) Activation of hydrolytic lignin obtained from corncobs", Kozharska i Obuvna Promishlenost, 13(6), 1972, 13-23.

Spigno et al., "(Abstract) Cellulose and hemicelluloses recovery from grape stalks", Bioresource Technology, 99(10), 2008, 4329-4337.

Springer, "(Abstract) Prehydrolysis of hardwoods with dilute sulfuric acid", Industrial & Engineering Chemistry Product Research and Development, 24(4), 1985, 614-23.

Srinivasan et al., "Pretreatment of Guayule Biomass Using Supercritical Carbon Dioxide-Based Method", Bioresource Technology, 101(24), 2010, 9785-9791.

Srokol et al., "(Abstract) Hydrothermal upgrading of biomass to biofuel; studies on some monosacchride model compounds", Carbohydrate Research, 339(10), 2004, 1717-1726.

Steinke, "(Abstract) Valve solutions for high-pressure letdown", Proceedings of the Symposium on Instrumentation for the Process Industries, 44th, 1989, 39-43.

Steinke et al., "(Abstract) Valve solutions for high pressure letdown", Advances in Instrumentation, 42(3), 1987, 1381-1390.

Strobel et al., "Carbohydrate Transport by the Anaerobic Thermophile Clostridium thermocellum LQRI", Applied and Environmental Microbiology, Nov. 1995, 4012-4015.

Suitor et al., "(Abstract) Development of a coal slurry letdown valve", American Society of Mechanical Engineers, Fluids Engineering Division, vol. 23, 1985, 142-144.

Sukhanovskii et al., "(Abstract) The chemical composition of the organic part and of ash in hydrolysis lignins", Gidroliznaya i Lesokhimicheskaya Promyshlennost, 18(5), 1965, 15-17.

Svitel'Skii, "(Abstract) Study of ash in lignin from kraft mill effluents", Mater. Nauch.-Tekh. Konf. Leningrad. Lesotekh. Akad., No. 4, 1966, 180-185.

Terol et al., "High-temperature liquid chromatography inductively coupled plasma atomic emission spectrometry hyphenation for the combined organic and inorganic analysis of foodstuffs", Journal of Chromatography, 1217(40), 2010, 6195-6202.

Trickett et al., "(Abstract) Dilute acid hydrolysis of bagasse hemicellulose", ChemSA, 8(3), 1982, 11-15.

Um et al., "Acid Hydrolysis of Hemicellulose in Green Liquor Pre-Pulping Extract of Mixed Northern Hardwoods", Appl. Biochem Biotechnol,153(1-3), 2009, 127-38.

Van Walsum et al., "(Abstract) Carbonic acid enhancement of hydrolysis in aqueous pretreatment of corn stover", Bioresource Technology, 93(3), 2004, 217-226.

Van Walsum, "(Abstract) Severity function describing the hydrolysis of xylan using carbonic acid", Applied Biochemistry and Biotechnology, 91-93, 2001, 317-329.

Varga et al., "(Abstract) Optimization of steam pretreatment of corn stover to enhance enzymatic digestibility", Applied Biochemistry and Biotechnology, 113-116, 2004, 509-523.

Veres et al., "(Abstract) Studies on matrix effects in the determination of the metal content of sugar complexes by atomic absorption spectrometry", Magyar Kemiai Folyoirat, 93(5), 1987, 199-204.

Vick Roy et al., "(Abstract) Biomass hydrolysis with sulfur dioxide and water in the region of the critical point", Process Technology Proceedings, 3 Supercrit. Flud Technol., 1985, 397-444.

Wu et al., "(Abstract) Determination of trace calcium in glucose by Zeeman flame atomic absorption spectrometry", Guangdong Weiliang Yuansu Kexue, 14(3), 2007, 58-60.

Yang et al., "(Abstract) Steaming extraction of corncob xylan for production of xylooligosaccharide", Wuxi Qinggong Daxue Xuebao, 17(4), 1998, 50-53.

Yee et al., "(Abstract) Improvement of xylose production by acid hydrolysis of bagasse pith with low liquor ratio", Taiwan Tangye Yanjiuso Yanjiu Huibao, 98, 1982, 59-70.

Yu et al., "(Abstract) Characteristics and Precipitation of Glucose Oligomers in the Fresh Liquid Products Obtained from the Hydrolysis of Cellulose in", Hot-Compressed Water, Industrial & Engineering Chemistry Research, 48(23), 2009, 10682-10690.

Zhang et al., "Cellulose utilization by *Clostridium thermocellum*: Bioenergetics and hydrolysis product assimilation", PNAS, May 17, 2005, 7321-7325.

Zhao et al., "(Abstract) Fermentable hexose production from corn stalks and wheat straw with combined supercritical and subcritical huydrothermal technology", Bioresource Technology, 100(23), 2009, 5884-5889.

Zhao et al., "(Abstract) Supercritical pretreatment and hydrolysis of cellulose", Huaxue Xuebao, 66(20), 2008, 2295-2301.

Zhao et al., "Combined supercritical and subcritical process for cellulose hydrolysis to fermentable hexoses", Environmental Science & Technology, 43(5), 2009, 1565-1570.

Zhuang et al., "(Abstract) Research on biomass hydrolysis under extremely low acids by HPLC", Taiyangneng Xuebao, 28(11), 2007, 1239-1243.

"Supercritical Fluids", Kirk-Othmer Encyclopedia of Chemical Technology, John Wiley & Sons, New York, Fifth Edition, vol. 22 (2006), 29 pages.

U.S. Appl. No. 12/504,611, "Final Office Action", mailed Jan. 30, 2012, 17 pages.

U.S. Appl. No. 12/504,611, "Final Office Action", mailed Jan. 18, 2013, 28 pages.

Chinese Patent Application No. 200980131809.5, "Office Action", mailed Dec. 25, 2012, 24 pages.

Ehara, "Chemical conversion of woody biomass by supercritical water—Degradation of Lignin—", 12th European Conference on Biomass for Energy, Industry and Climate Protection, Amsterdam, The Netherlands, 2002, 2 pages.

\* cited by examiner

SOLVO-THERMAL HYDROLYSIS OF CELLULOSE

CROSS-REFERENCE TO RELATED APPLICATIONS

This application claims priority to U.S. Provisional Patent Application No. 61/081,337 filed Jul. 16, 2008, U.S. Provisional Patent Application No. 61/081,341 filed Jul. 16, 2008, U.S. Provisional Patent Application No. 61/081,348 filed Jul. 16, 2008, U.S. Provisional Patent Application No. 61/092,680 filed Aug. 28, 2008, and U.S. Provisional Patent Application No. 61/224,809 filed Jul. 10, 2009, the disclosures of each of which are incorporated herein by reference in their entireties. This application is related to and incorporates by reference the following PCT application filed on even date herewith: "NANO-CATALYTIC-SOLVO-THERMAL TECHNOLOGY PLATFORM BIO-REFINERIES", inventors Srinivas Kilambi and Kiran L. Kadam.

STATEMENT OF RIGHTS TO INVENTIONS MADE UNDER FEDERALLY SPONSORED RESEARCH

Not applicable.

BACKGROUND OF THE INVENTION

Cellulose is a valuable renewable energy resource. Glucose, fructose and their oligomers which can be obtained by the hydrolysis of cellulose are expected to be valuable chemicals, food and feed stock.

Various methods using acid catalyst or enzyme have been proposed for the hydrolysis of cellulose to recover glucose. It was reported that the low temperature (100-120° C.) concentrated acid hydrolysis of cellulose provided glucose yields approaching 100%. Acid hydrolysis of cellulose in high temperature water produced 71% of theoretical maximum yield of glucose. The process conditions were 215° C., 34.5 MPa and 120 min with 0.05 wt % sulfuric acid.

Supercritical and near supercritical fluids have been described for processing cellulosic materials, e.g. recycling cellulose esters from the waste from cigarette manufacture (U.S. Pat. No. 5,328,934); removing adhesives from cellulose (U.S. Pat. No. 5,009,746); extracting terpenes and oils from wood (U.S. Pat. No. 4,308,200); removing lignin from Kraft streams (U.S. Pat. No. 4,493,797); removal of the natural oils from plant matter (U.S. Pat. No. 4,675,198) and forming cellulose acetate articles (U.S. Pat. No. 5,512,231).

Examples of other related references are: Sasaki et al. "Cellulose hydrolysis in sub-critical and supercritical water" *Journal of Supercritical Fluids* (1998) 13:261-268; and Adschiri et al. "Noncatalytic Conversion of Cellulose in Supercritical and Sub-critical Water" *Journal of Chemical Engineering of Japan* (1993) 26(6):676-680. Miyazawa et al. report a 14-fold increase in glucose yield with $CO_2$ addition at sub-critical water conditions (200° C. for 15 min residence time).

Commercial applications of supercritical fluid extraction include the decaffeination of coffee and tea; extraction of hops flavors for beer manufacture; and denicotination of tobacco. Such commercial processes have been used and are described in reviews such as: McHugh and Krukonis, Supercritical Fluid Extraction: Principles and Practice, Butterworths, (1986); Eckert et al., *Environmental Science and Technology*, Vol. 20, pp. 319-325, (1986); "Supercritical Fluids", Kirk-Othmer Encyclopedia of Chemical Technology 3$^{rd}$ ed., John Wiley & Sons, New York.

All patents, patent applications, documents, and articles cited herein are herein incorporated by reference in their entirety.

BRIEF SUMMARY OF THE INVENTION

Disclosed are various methods, apparatus configurations, and compositions involved in converting biomass to more valuable products.

The cellulose produced by supercritical fractionation of biomass, amorphous and/or crystalline, may be used alone or together with additional cellulose to produce glucose and/or fructose. In one instance, a method involves contacting cellulose with carbon dioxide and water at a temperature and pressure above the critical point for carbon dioxide and below the critical point for water, e.g. sub-critical or near-critical water. In another instance, a method involves contacting cellulose with carbon dioxide and water at a temperature and pressure at, above or near the critical point water, e.g. supercritical or near-critical water. The method may involve contacting the cellulose for a sufficient period of time to obtain glucose and optionally fructose.

In another instance, a method involves contacting cellulose first with supercritical water and subsequently contacting the resultant slurry with carbon dioxide and water at a temperature and pressure above the critical point for carbon dioxide and below the critical point for water. The method may involve contacting the cellulose for a sufficient period of time to obtain glucose and optionally fructose.

Also provided is a process for hydrolyzing cellulose, comprising: (a) supplying a slurry comprising cellulose, water and $CO_2$ at a first temperature; (b) heating the slurry at a second temperature and a pressure for a first time period, wherein the $CO_2$ is supercritical $CO_2$ and the water is near-critical or supercritical water, and wherein a hydrolysis reaction occurs; (c) quenching the reaction; and (d) recovering at least one hydrolysis product. In some embodiments, the first temperature is about 220 to about 280° C. In some embodiments, the second temperature is about 371 to about 377° C. In some embodiments, the pressure is about 225 bar. In some embodiments, the first time period is about 0.12 to about 0.3 seconds. In some embodiments, the cellulose solids remaining after the first pass is recovered and subject to another round of hydrolysis using any method for cellulose hydrolysis described herein. In some embodiments, the cellulose solids remaining after the first pass is not recovered and the mixture is treated with supercritical $CO_2$ and sub-critical water to achieve further hydrolysis and better yield of glucose.

In one instance, a system for hydrolyzing cellulose to form glucose, and optionally fructose, comprising: a reactor configured for contacting cellulose with a reactive fluid at a temperature and pressure above the critical point of carbon dioxide but at least one of the temperature and pressure of the fluid is beneath the critical temperature and pressure for water; a heating device configured for heating the reactive fluid to the desired temperature; a back-pressure regulator located downstream of the reactor for maintaining the desired pressure; and a heat exchanger configured for cooling the reaction and located downstream of the reactor. In some embodiments, the system may further comprise a filtration device configured for separating at least a portion of the fractionated product in solid state from the fractioned and cooled reaction mixture.

A composition may comprise cellulose and/or glucose in a mixture of carbon dioxide and water at a temperature and pressure above the critical point for carbon dioxide and below the critical point for water. A composition may comprise cellulose and/or glucose in a mixture of carbon dioxide and water at a temperature and pressure at, above or near the critical point water. A composition may comprise carbon dioxide and glucose in water, wherein the temperature and pressure are below the critical point for carbon dioxide and water.

Also provided is a composition as described herein, including reaction intermediates as described, or a product produced by any of the processes as described herein or a portion of the processes described. Also provided is a system for producing any of the compositions described herein, or for performing any of the methods or a portion of a method as described herein.

Other methods and compositions are apparent from the disclosure herein.

DETAILED DESCRIPTION OF THE INVENTION

Figure 1:
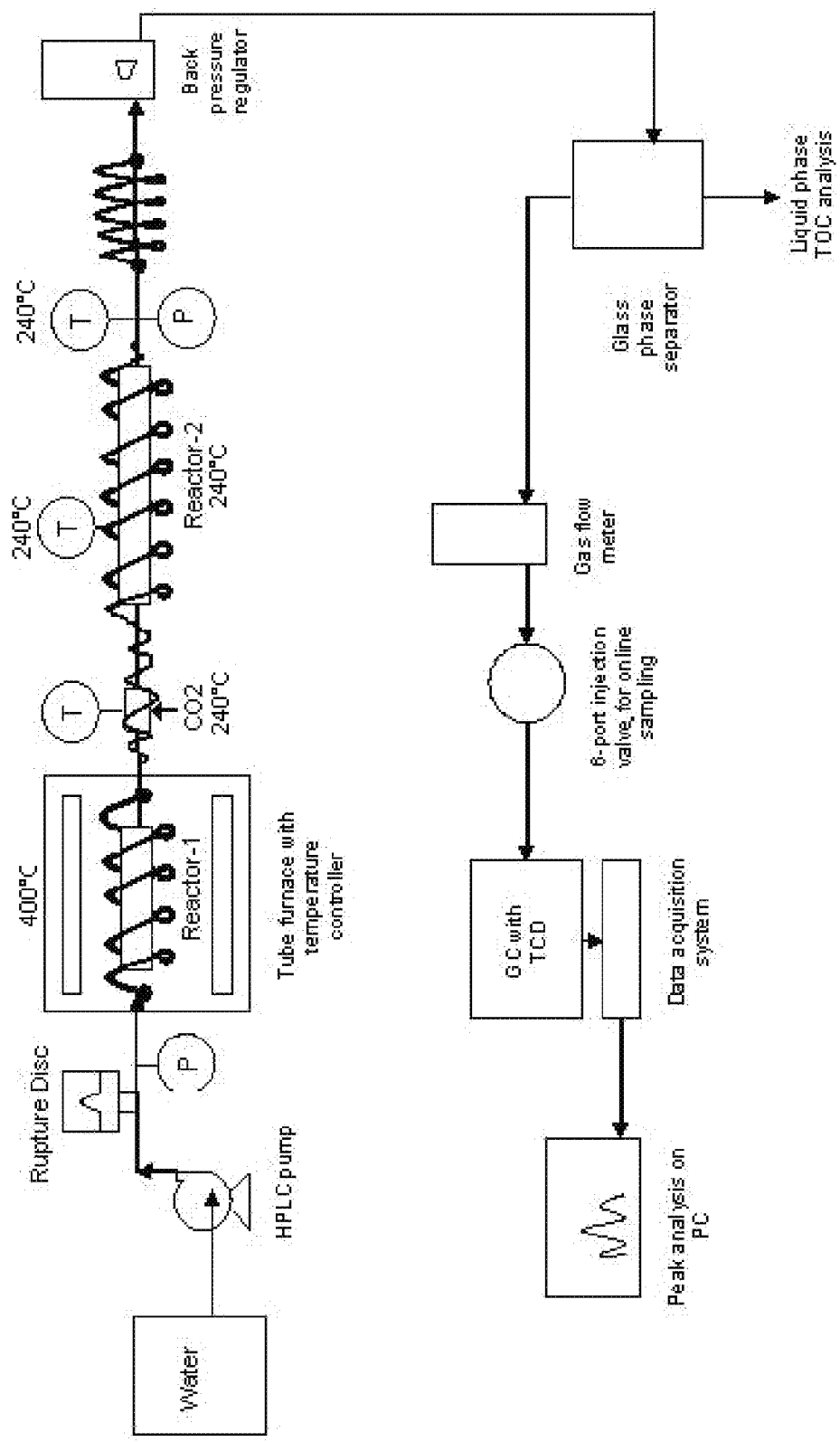
FIG. 1 depicts a schematic of an example of an apparatus used in a process for semi-continuous cellulose hydrolysis.

The Nano Carbonic Solvothermal Technology (NCST) of this invention provides methods for performing cellulose hydrolysis in sub- or near-critical water and carbon dioxide. Optionally, the cellulose may be solubilized with near critical or supercritical water prior to hydrolysis.

A supercritical fluid is a fluid at a temperature above its critical temperature and a pressure above its critical pressure. A supercritical fluid exists at or above its "critical point", the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good salvation. Typical near-critical and supercritical aqueous phases have temperatures in the range from about 250° C. to about 500° C. (or higher) and pressures greater than about 200 bar. The critical temperature for pure water is 374.2° C., and its critical pressure is 221 bar. Carbon dioxide has a critical point of 31° C. and 72.9 atmospheres (about 1072 psig).

Near-critical water has a temperature at or above about 300° C. and below the critical temperature, and near-critical water has a pressure of at least about 225 bar. Sub-critical water has a temperature of less than about 300° C. and a pressure of at least about 225 bar. Sub-critical water temperature may be greater than about 250° C. and less than about 300° C., and in many instances sub-critical water has a temperature between about 250° C. and about 280° C.

As used herein, a fluid which is "supercritical" (e.g. supercritical water, supercritical ethanol, supercritical $CO_2$, etc.) indicates a fluid which would be supercritical if present in pure form under a given set of temperature and pressure conditions. For example, "supercritical water" indicates water present at a temperature of at least about 374.2° C. and a pressure of at least about 221 bar, whether the water is pure water, or present as a mixture (e.g. water and ethanol, water and $CO_2$, etc). Thus, for example, "a mixture of sub-critical water and supercritical carbon dioxide" indicates a mixture of water and carbon dioxide at a temperature and pressure above that of the critical point for carbon dioxide but below the critical point for water, regardless of whether the supercritical phase contains water and regardless of whether the water phase contains any carbon dioxide. For example, a mixture of sub-critical water and supercritical $CO_2$ may have a temperature of about 250° C. to about 280° C. and a pressure of at least about 225 bar.

Mechanism of Cellulose Hydrolysis

Cellulose is composed of long chains of sugar molecules of various kinds. Each cellulose molecule is an unbranched polymer of 1000 to 1 million D-glucose units, linked together with beta-1,4-glycosidic bonds. Cellulose from various sources are all the same at the molecular level. In the hydrolysis process, these chains are broken down to free the sugar.

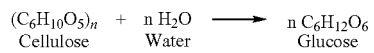

$$(C_6H_{10}O_5)_n + n\,H_2O \longrightarrow n\,C_6H_{12}O_6$$
$$\text{Cellulose} \quad\quad \text{Water} \quad\quad\quad\quad \text{Glucose}$$

There are two types of hydrogen bonds in cellulose molecules: those that form between the C3-OH group and the oxygen in the pyranose ring within the same molecule and those that form between the C6-OH group of one molecule and the oxygen of the C3-OH group of another molecule. Ordinarily, the beta-1,4-glycosidic bonds themselves are not too difficult to break. However, because of the hydrogen bonding network, cellulose can form very tightly packed crystallites. These crystals are sometimes so tight that neither water nor enzyme can penetrate them; only exogluconase, a subgroup of cellulase that attacks the terminal glucosidic bond, is effective in breaking it down. The inability of water to penetrate cellulose also explains why crystalline cellulose is insoluble. On the other hand, amorphous cellulose allows the penetration of endogluconase, another subgroup of cellulase that catalyzes the hydrolysis of internal glycosidic bonds. The natural consequence of this difference in the crystalline structure is that the hydrolysis rate is much faster for amorphous cellulose than that for crystalline cellulose. The process of breaking the glucosidic bonds that hold the glucose basic units together to form a large cellulose molecule is called hydrolysis because a water molecule must be supplied to render each broken bond inactive.

The inability of the water to penetrate cellulose may be overcome by penetrating the water at supercritical or near-critical conditions. The supercritical water breaks down the hydrogen bonds of crystalline structure cellulose, solubilizing the cellulose.

Supercritical water can lead to complete hydrolysis of cellulose, but typically the glucose and fructose yields are around 25% and 13%, respectively. The addition of $CO_2$ increases these yields and provides a fast process for converting cellulose to glucose and fructose, for instance. Supercritical carbon dioxide reacts with sub-critical or near-critical water to form carbonic acid. The carbonic acid acts as an acid-catalyst in hydrolysis of the glucosidic bonds in cellulose to produce glucose, fructose, mannose, and oligomers thereof. Supercritical $CO_2$ mixed with sub-critical, near-critical or supercritical water catalyzes the hydrolysis of cellulose but has minimal impact on the decomposition of the hydrolysis products (e.g. glucose and fructose). Consequently, while a strong acid such as a mineral acid may be used in certain instances, often it is not needed or used in a method disclosed herein.

The near-critical or supercritical water solubilization initially results in rapid complete solubilization of cellulose, to give a solution of highly water soluble compounds (oligomers). This is followed by a temperature reduction step (to sub-critical or near-critical water conditions) in combination with $CO_2$ injection to increase the hydrolysis pathway to the sugars in high yield. Hydrolysis in the near critical water region without $CO_2$ is problematic, as the reaction rate decreases, requiring long residence times which can lead to the formation of undesirable decomposition products that can inhibit downstream fermentation.

Nano Carbonic Hydrothermal Treatment

The invention provides a process for cellulose hydrolysis using the Nano Carbonic Solvothermal Technology (NCST), in which supercritical carbon dioxide and sub-critical, near-critical or supercritical water are used in a solvothermal process. The reaction may be performed as a single stage (hydrolysis only) or a two-stage (solubilization and hydrolysis) reaction.

The single-stage process for hydrolyzing cellulose may be generally as follows: cellulose is contacted with a fluid mixture comprising supercritical $CO_2$ and sub-critical or near-critical water to form a reactant mixture at a hydrolysis temperature and hydrolysis pressure for a hydrolysis time period (e.g. the residence time in a reactor), wherein a reaction occurs and forms one or more hydrolysis products; and then the reaction is quenched. One or more hydrolysis products (e.g. glucose, fructose, mannose, cellobiose, and oligomers) may be obtained and recovered from the reaction.

In a two stage process for cellulose hydrolysis, the cellulose is solubilized prior to the hydrolysis. The two-stage process may be generally as follows: (1) cellulose is solubilized by contacting the cellulose with near-critical or supercritical water at a solubilization temperature and a solubilization pressure for a solubilization time period (e.g. the residence time in a reactor); and (2) the solubilization reaction is quenched. The solubilized cellulose is then contacted with a fluid mixture comprising supercritical $CO_2$ and sub-critical or near-critical water to form a reactant mixture at a hydrolysis temperature and hydrolysis pressure for a hydrolysis time period (e.g. the residence time in a reactor), wherein a reaction occurs and forms one or more hydrolysis products; and then the reaction is quenched. One or more hydrolysis products (e.g. glucose, fructose, mannose, cellobiose, and oligomers) may be obtained and recovered from the reaction. While the first stage (the solubilization stage) is optional, the two stage process may in some embodiments provide higher product yields than the single stage process.

The cellulose used in this invention can be obtained from various sources and in various forms, e.g. α-cellulose fibers, bleached cotton (natural cellulose), and cellulose produced from fractionation of a biomass, e.g. a lingo-cellulosic biomass such as wood, corn stover, wheat straw, bagasse, solid organic waste and the like. In one embodiment, the cellulose is obtained from a biomass fractionation process according to the methods described in U.S. Patent Application Ser. No. 61/081,337 filed on Jul. 16, 2008, the disclosure of which is herein incorporated by reference in its entirety. The cellulose may optionally be made into a slurry prior to the solubilization and/or hydrolysis reaction, by combining with one or more fluids such as water. In some embodiments, the slurry comprises about ½ to about 20 wt % cellulose. In some embodiments, the slurry comprises about 1 to about 10 wt % or 5 wt % cellulose. The cellulose may be crystalline or amorphous.

Solubilizing Cellulose

Cellulose may be solubilized in water with or without added materials. For instance, if desired, one may first dissolve a crystalline cellulose using the appropriate enzyme as discussed above. However, in many instances, an enzyme is unnecessary. Cellulose may be dissolved in water that is below the supercritical point, such as in sub-critical or near-critical water. Cellulose may be dissolved in supercritical water instead of or in addition to dissolving it in water below the supercritical point.

Consequently, the solubilization temperature for cellulose may be about, for example, about 373° C. to about 420° C. In some embodiments, the solubilization temperature is about 375° C. to about 400° C. In some embodiments, the solubilization temperature is about 375° C. In some embodiments, the solubilization is performed with supercritical water. In some embodiments, the solubilization is performed with near critical water. Generally, using near critical water for solubilization may require longer solubilization time periods to achieve an equivalent level of solubilization in comparison with using supercritical water. In the solubilization step, supercritical water forms a homogeneous mixture with cellulose and causes its complete solubilization in very short time (c.<1 sec). However, the initial hydrolysis products are further decomposed at supercritical temperatures. In near-critical water, both the hydrolysis of cellulose and further decomposition of the hydrolysis product are slower. Prolonged treatment with near-critical water tends to result in significant amount of undesirable decomposition products (glycoaldehydes, erthsose, glyceraldehydes, etc).

The solubilization pressure may be about, for example, 221 bar to about 350 bar. In some embodiments, the solubilization pressure is about 200 bar to about 240 bar. In some embodiments, the solubilization pressure is about 200 bar to about 225 bar. In some embodiments, the solubilization pressure is about 225 bar. In some embodiments, the solubilization pressure is about 225 bar, and the solubilization temperature is about 375° C.

Solubilization may therefore be just below the supercritical point, at or slightly above the supercritical point, or at any combination of the temperature and pressure ranges discussed above.

The solubilization time period may be about, for example, about 0.1 s to about 5 s; these time period are based on water density at process conditions. In some embodiments, the solubilization time period is about 0.1 s to about 2 s. In some embodiments, the solubilization time period is about 0.1 s to about 1 s. In some embodiments, the solubilization time period is about 1 s to about 2 s. In some embodiments, the solubilization time period is about 0.5 s. Solubilization is preferably performed quickly when supercritical water is used, and longer time periods are often used when near-critical or sub-critical water are used.

The solubilization reaction may be quenched immediately by reducing the temperature of the reaction, e.g. to 250-350° C. to minimize hydrolyzing desired products made in the solubilizing step. In some embodiments, the solubilization reaction is quenched by reducing the temperature to about 280-290° C. The temperature may be reduced, for example, by addition of a cooler fluid (e.g. $CO_2$, water, or a combination of $CO_2$ and water). In some embodiments, the amount of $CO_2$ added to quench results in a mixture containing about 5 wt % to about 20 wt % $CO_2$ of the total fluids. In some embodiments, the $CO_2$ is supercritical $CO_2$.

In some embodiments, process cellulose is diluted in a 1:1 ratio with water, the mixture is heated rapidly to 375° C. so that the water is in supercritical condition, and the pressure is maintained at 225 to 300 bar. In one such embodiments, process cellulose slurry at 220° C. is diluted in a 1:1 ratio with water at 440° C., thereby rapidly heating the mixture to 375° C. so that the water is in supercritical condition; the pressure is maintained at 225 to 300 bar. After about ½-1 sec, the mixture is quenched to about 280-300° C.

Hydrolysis Reaction

As noted previously, the cellulose solubilization step above does not occur for a single-step solubilization-hydrolysis process. A fluid mixture comprising supercritical $CO_2$ and water at, above, or below its critical point is used to both solubilize and hydrolyze cellulose simultaneously rather than having steps designed to perform primarily solubilization and primarily hydrolysis. The fluid mixture reacts with cellulose for a sufficient period of time to dissolve cellulose and convert at least a portion of it to desired products such as glucose and fructose. For a single-step solubilizing-hydrolysis process, generally the rate-limiting step is the rate of dissolving cellulose, and consequently conditions are selected as outlined below to provide longer reaction times but lower temperatures to avoid e.g. hydrolysis or degradation of desired products to side or unwanted products.

Generally, the fluid mixture in the hydrolysis reaction may comprise about 1-30 wt % of $CO_2$. In some embodiments, the fluid mixture comprises about 5 wt % to about 20 wt % $CO_2$. In some embodiments, the fluid mixture is saturated with $CO_2$. The $CO_2$ may be combined with the water prior to contacting with the cellulose, or may be contacted with the cellulose separately from the water (e.g. through different reaction injection ports in a reactor). Alternatively, water may be carried over from the solubilizing step. In some embodiments, the hydrolysis reaction is performed at a pH of about 3 to about 5 by adjusting the amounts of $CO_2$ and water as needed.

The hydrolysis temperature may be about, for example, 270° C. to about 340° C. In various embodiments, the hydrolysis temperature may be about, for example, about 270° C. to about 300° C., about 280° C. to about 320° C., about 280° C. to about 300° C., about 280° C. to about 290° C., about 280° C., or about 300° C.

The hydrolysis pressure may be about, for example, 180 bar to about 350 bar. In various embodiments, the hydrolysis pressure is about 180 bar to about 225 bar, about 200 bar to about 225 bar, or about 225 bar.

Conditions may be selected so that the temperature and pressure are near-critical or sub-critical for the water of the hydrolyzing fluid.

The hydrolysis time period may be about for example, about 1 s to about 30 s. In general, when performing a single-stage reaction, the hydrolysis time period will be longer than when performing a two-stage reaction. Generally, the two-stage reaction will result in higher yields with much shorter reaction times. In various embodiments, the hydrolysis time period is, for example, about 2 s to about 30 s, about 2 s to about 3 s, about 3 s to about 15 s, about 15 s to about 20 s.

In one instance, supercritical $CO_2$ and sub-critical water hydrolyze cellulose at a temperature of about 280-290° C. and a pressure of about 225 bar for a period of about 15-20 seconds. These conditions allow the process to be easily controlled, but at the expense of slight loss or conversion of desired product (e.g. glucose, fructose) to side or unwanted product (e.g. acetic and propionic acid).

In another instance, hydrolysis may be performed first at conditions where both water and $CO_2$ are at or above their respective critical points to perform a rapid hydrolysis on dissolved cellulose, followed by immediate reduction in temperature to milder conditions as discussed in the paragraph above to complete the reaction. For example, supercritical water and supercritical $CO_2$ hydrolyze the dissolved cellulose for a period of about ¼-1 sec., preferably about ¼-½ sec. or about 0.6-0.8 sec. at a temperature of about or slightly above the critical temperature and a pressure of about or slightly above the critical pressure (e.g. about 374 or 375° C. and about 223-225 bar). The mixture is immediately quenched by e.g. introducing cooler water and $CO_2$ to reduce the temperature below the critical temperature and react instantaneously, for a period of less than 5 sec., between about 1-5 sec., or about 2-3 sec. These conditions provide for a faster reaction time than the single step hydrolysis process discussed above while providing about the same or better product yield.

The hydrolysis reaction may be quenched by a variety of methods, such as adding a cooler fluid (e.g. water) directly to the reactant mixture, by indirect cooling (heat exchange), or by performing work on a turbine. In some embodiments, the hydrolysis reaction is quenched by cooling the reactant mixture to a temperature of about 30° C. to about 80° C., about 20° C. to about 80° C., about 25° C., or about room temperature.

One or more hydrolysis products (e.g. glucose, fructose, mannose, cellobiose, cellotriose, and oligomers may be obtained and recovered from the reaction. The particular reaction products obtained depend upon the content of the original biomass as well as the reaction conditions used to hydrolyze the cellulose. For example, mannose may be obtained from particular types of biomass, such as softwoods, hemicellulose of which contains mannans. Glucose is the sugar monomer in cellulose, which is released upon hydrolysis. Fructose is formed by isomerization of glucose under certain reaction conditions. Higher levels of fructose (versus glucose) may be selected for when using higher hydrolysis pressures (e.g. greater than 300 bar, about 350 bar). Oligomers may be obtained when cellulose is partially hydrolyzed. In some embodiments, the at least one hydrolysis product is selected from the group consisting of glucose, fructose, and oligomers thereof. In some embodiments, the at least one hydrolysis product is glucose. In some embodiments, the at least one hydrolysis product is fructose. In some embodiments, the at least one hydrolysis product is mannose. In some embodiments, the at least one hydrolysis product is cellobiose. The hydrolysis products may be analyzed by conventional methods, such as e.g. HPLC, and may be separated by conventional methods.

Figure 4:
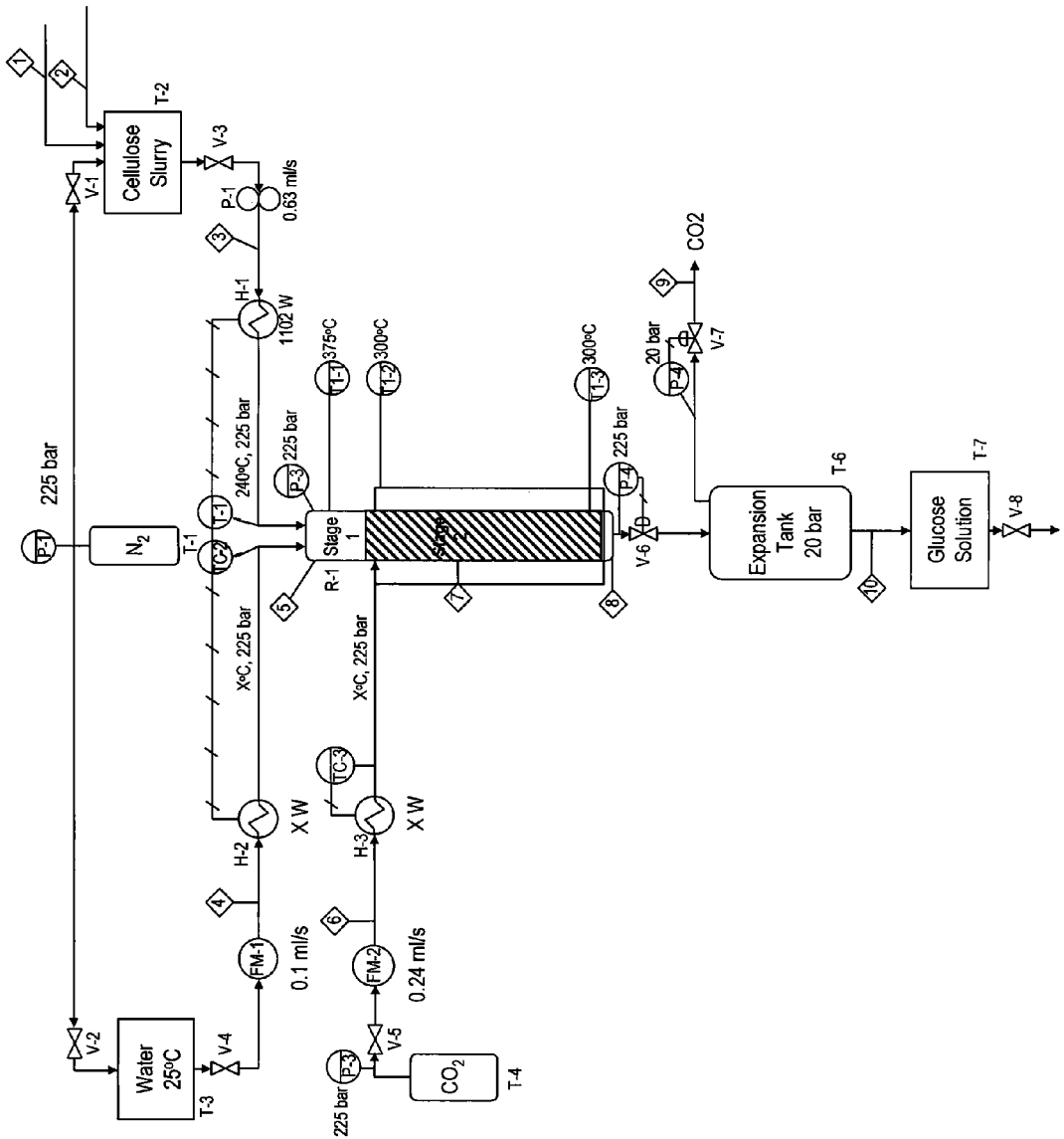
FIG. 4 depicts an example of a reactor system for a continuous two-stage process for cellulose hydrolysis in the Nano Carbonic Solvothermal Technology (NCST) process.

The process may be a batch process in which all fluids and reactants enter the reactor and are retained there without further addition, a semi-continuous process in which e.g. cellulose is placed in a reactor and a dissolving and/or hydrolyzing fluid passes through the bed or mass of cellulose, or a continuous process in which cellulose and fluids are constantly added, and may utilize conventional chemical reactor technology. FIG. 4 is a schematic of one example of a reactor for a continuous two-stage reaction process.

In some embodiments, the process is a semi-continuous process for cellulose hydrolysis comprising: (a) adding the cellulose to a first reactor that is maintained at a first constant temperature; (b) continuously pumping water through the first reactor; (c) solubilizing the cellulose in the first reactor; (d) quenching the solubilization reaction; (e) transferring the solubilized cellulose to a second reactor; (f) contacting the solubilized cellulose with $CO_2$ in the second reactor; (g) hydrolyzing the solubilized cellulose in the second reactor to form one or more hydrolysis products; (h) continuously removing the one or more hydrolysis products from the second reactor; (i) rapidly cooling and depressurizing the one or more hydrolysis products; and (j) recovering at least one hydrolysis product.

In some embodiments, the process is a continuous process for cellulose hydrolysis comprising: (a) mixing the cellulose with water to form a slurry; (b) continuously pumping the cellulose slurry through a first reactor that is maintained at a constant first temperature; (c) solubilizing the cellulose in the first reactor; (d) transferring the solubilized cellulose slurry and the $CO_2$ to a second reactor; (f) hydrolyzing the solubilized cellulose in the second reactor to form one or more hydrolysis products; (g) continuously removing the one or more hydrolysis products from the second reactor; (h) rapidly cooling and depressurizing the one or more hydrolysis products; and (i) recovering at least one hydrolysis product. In some embodiments, the residence time of the cellulose slurry in the first reactor is adjusted by varying the flow rate of the cellulose slurry through the first reactor.

In some embodiments, the process comprises: solubilizing cellulose with supercritical water at about 375° C. and about 225 bar for about 1 to about 2 seconds or about 0.6 to about 2 seconds; quenching the solubilization reaction; hydrolyzing the cellulose using supercritical carbon dioxide and near-critical water at about 300° C. and about 200 bar or 220 bar to about 225 bar for about 2 to 30 seconds; quenching the hydrolysis reaction mixture; and recovering at least one hydrolysis product. In some embodiments, the at least one hydrolysis product is selected from the group consisting of glucose, fructose, and oligomers.

The invention also provides a continuous process for hydrolyzing cellulose to produce valuable products such as glucose and fructose comprising: (a) supplying a slurry comprising cellulose, water and $CO_2$ at a first temperature; (b) heating the slurry at a second temperature and a pressure for a first time period, wherein a reaction occurs and forms one or more hydrolysis products; (c) quenching the reaction; and (d) recovering at least one hydrolysis product. The slurry is supplied at a temperature of about 220 to about 280° C., e.g. at about 220° C., about 250° C. or about 280° C. The hydrolysis reaction is carried out at a temperature near or at the critical temperature of water. In some embodiments, the second temperature is about 371 to about 377° C., e.g. at about 371° C., at about 372° C., at about 373° C., at about 374° C., at about 375° C., about 376° C. or about 377° C. In one embodiment, the pressure is maintained at 225 bar. The residence time of the mixture of cellulose, supercritical $CO_2$ and supercritical water in the reactor where hydrolysis occurs is calculated based on water density at process conditions and the flow rate. In some embodiments, the first time period is about 0.12 to about 0.3 seconds.

Also provided is a system for hydrolyzing cellulose to form glucose, and optionally fructose, comprising a reactor configured for contacting cellulose with a reactive fluid at a temperature and pressure above the critical point of carbon dioxide but at least one of the temperature and pressure of the fluid is beneath the critical temperature and pressure for water. In some embodiments, the system comprises a reactor configured for contacting cellulose with a reactive fluid at a temperature and pressure at, above or near the critical point water. In some embodiments, the reactor is configured for contacting cellulose with a reactive fluid at a temperature of up to about 250° C., about 300° C., about 350° C., about 375° C. or about 400° C. and a pressure of up to about 100 bar, about 150 bar, about 200 bar, about 250 bar, about 300 bar, or about 350 bar. In some embodiments, the system further comprises a heating device configured for heating the reactive fluid to the desired temperature and a back-pressure regulator located downstream of the reactor for maintaining the desired pressure. In some embodiments, the system may further comprise a heat exchanger configured for cooling a reaction located downstream of the reactor. In some embodiments, the system may further comprise a filtration device configured for separating solids and particulate matters from liquids in a reaction mixture, such as a high-pressure filter. In some embodiments, the system may further comprise a second reactor configured for solubilizing cellulose in a reactive fluid at a temperature and pressure above the critical point of carbon dioxide but at least one of the temperature and pressure at, above or near the critical point water.

In some embodiments, the system for hydrolyzing cellulose to form glucose, and optionally fructose, may further comprise additional apparatus such as vessels for holding the fluids or slurry, devices for monitoring the temperatures and pressures, and modules for date collection and safety controls. In some embodiments, the system may further comprise a composition comprising cellulose and/or glucose, water, and optionally $CO_2$.

In some embodiments, the invention provides a composition comprising cellulose and/or glucose in a mixture of carbon dioxide and water at a temperature and pressure above the critical point for carbon dioxide and below the critical point for water. In some embodiments, the composition comprises cellulose, $CO_2$ and water at about 100° C. to about 375° C. In some embodiments, the composition comprises cellulose, $CO_2$ and water at about 100° C. to about 300° C. In some embodiments, the composition comprises cellulose, $CO_2$ and water at about 200° C. to about 375° C. In some embodiments, the composition comprises cellulose, $CO_2$ and water at about 100° C. to about 375° C. and about 100 to about 350 bars. In some embodiments, the composition comprises about 3 wt % to about 5 wt % cellulose. In some embodiments, the composition comprises cellulose, glucose, $CO_2$ and water at about 100° C. to about 375° C. In some embodiments, the composition comprises cellulose, glucose, $CO_2$ and water at about 100° C. to about 375° C., about 100° C. to about 300° C., 200° C. to about 375° C. In some embodiments, the composition comprises cellulose, glucose, $CO_2$ and water at about 100° C. to about 375° C. and about 100 to about 350 bars. In some embodiments, the composition comprises glucose, $CO_2$ and water at about 100° C. to about 375° C. and about 100 to about 350 bars. In various embodiments, the composition may comprise, for example, about 5 wt % to about 20 wt % $CO_2$.

In some embodiments, the invention provides a composition comprising a product of cellulose hydrolysis following any of the process for hydrolyzing cellulose or any variations thereof described herein. In some embodiments, the composition comprises a glucose product produced in a process for hydrolyzing cellulose or any variations thereof described. In some embodiments, the composition comprises a fructose product produced in a process for hydrolyzing cellulose or any variations thereof described. In some embodiments, the composition comprises a glucose product and a fructose product produced in a process for hydrolyzing cellulose or any variations thereof described.

The practice of this invention can be further understood by reference to the following examples, which are provided by way of illustration and are not intended to be limiting.

EXAMPLES

Example 1

A Semi-Continuous Process for Cellulose Hydrolysis

An apparatus for semi-continuous cellulose solubilization and hydrolysis was designed and constructed. A schematic of the apparatus is shown in FIG. 1.

Cellulose was packed in the first reactor, which was maintained at a constant temperature. Water was continuously pumped through the reactor to solubilize the cellulose and to carry the solubilized cellulose and water to the second reactor, in which $CO_2$ was added for hydrolysis. Formed products were continuously removed from the reactor, rapidly cooled and depressurized. The gaseous and liquid products were phase separated.

α-Cellulose fibers and bleached cotton (natural cellulose) were obtained from commercial sources. Cellulose from corn stover was produced using the process as described in U.S. Provisional Patent Application No. 61/081,337 filed on Jul. 16, 2008. Water was purified using a Barnstead NANOpure Infinity® purification system, and $CO_2$ was acquired from Airgas.

The reaction conditions were: 225 bar pressure, 10 mL volume Reactor-1, 2 mL volume Reactor-2, 375° C. for cellulose solubilization in an oven heated to 400° C., 1 second reaction time and 300° C. for cellulose hydrolysis (8 seconds reaction time).

Typically, Reactor-1 was packed with cellulose and placed inside the furnace, followed by the following steps: (i) Water flow started at desired flow rate using high pressure pump. (ii) Reactor-2 and inlet line of $CO_2$ heated to 300° C. (iii) $CO_2$ flow started at desired flow rate. (iv) After stabilizing the temperature of Reactor-2 at 300° C., the furnace to heat Reactor-1 to 375° C. was started. (v) Liquid product samples were collected at desired intervals from phase separator.

Sugar analysis was done using HPLC, using column Bio-Rad Aminex HPX-87P (Lead based column), RI detector, at 85° C., with water as the mobile phase. Known concentrations of glucose, fructose and cellobiose were injected in the column for calibration.

(a) Hydrolysis of Bleached Cotton (Natural Cellulose)

Three experiments were conducted using bleached cotton at the water flow rates of 5.0, 7.5 and 10.0 gm/min for the process conditions are shown in Table 1.

TABLE 1

Reaction conditions and maximum TOC observed for natural cellulose.

| Experiment ID | Initial mass of bleached cotton (mg) | Water inlet rate (g/min) | $CO_2$ inlet rate (g/min) | Residence time, (seconds) $\tau_1$ | $\tau_2$ | Maximum TOC observed (ppm) |
|---|---|---|---|---|---|---|
| E111607 | 518.0 | 10 | 1 | 1.3 | 3.6 | 215 |
| E111907 | 647.0 | 5 | 2 | 3.1 | 4.4 | 4944 |
| E111907A | 491.1 | 7.5 | 2 | 1.6 | 3.6 | 297 |

For experiment E111907, liquid product with a surge in total organic compound (TOC obtained at 15 minutes, the liquid volume was 135 ml) was analyzed. This liquid contained glucose, cellobiose and traces of oligomers. Glucose and cellobiose concentrations were determined as 0.83 g/l and 0.27 g/l, respectively, which correspond to yields of 16% glucose and 5.3% cellobiose.

(b) Hydrolysis of α-Cellulose

Two experiments were conducted using α-cellulose fibers procured from Sigma-Aldrich with the following specifications: Product Number: C8002; Appearance: white to off-white powder; Bulk density (g/ml): 0.23 to 0.32; Mesh (% retained): max. 20.0; 100 mesh (% passing): min. 50.0; 200 mesh (% passing): min. 35.0.

For experiment no. E112807, reactor-1 dimensions were ¼" inner diameter (ID)×6" long. For experiment no. E113007, reactor-1 dimensions were 5/16" ID×4" long.

TABLE 2

Reaction conditions and maximum TOC observed for α-cellulose.

| Experiment ID | Initial mass of cellulose (mg) | Water inlet rate (g/min) | $CO_2$ inlet rate (g/min) | Residence time, (seconds) $\tau_1$ | $\tau_2$ | Maximum TOC observed (ppm) |
|---|---|---|---|---|---|---|
| E112807 | 738.1 | 5 | 2 | 0.6 | 4.4 | 4388 |
| E113007 | 2004.1 | 5 | 2 | 3.8 | 4.4 | 3084 |

Dissolved solids in product solution were observed during both the experiments. These solids were filtered using Whatman paper, and the filtrate was analyzed in HPLC for glucose and cellobiose concentration.

TABLE 3

Results using α-cellulose.

| Experiment ID | Glucose conc. (g/l) | Cellobiose conc. (g/l) | Weight of dissolved solid (mg) | Volume of filtered product liquid (ml) |
|---|---|---|---|---|
| E112807 | 1.36 | 0.39 | 87.00 | 25 |
| E113007 | 0.80 | 0.45 | 690.19 | 79 |

After the reaction in experiment E112807, about 10 wt % of the α-cellulose fibers were found as a solid residue in reactor-1. Liquid product of E113007 was colorless. Highest concentration of glucose, 1.52 g/l, was observed after 15 min, and the highest concentration of cellobiose, 0.94 g/l was observed after 10 min of the startup in the E113007 experiment.

(c) Hydrolysis of De-Lignified Corn Stover:

Two experiments, E 122107 and E 122207, were conducted using de-lignified corn stover produced using the process as described in U.S. Provisional Patent Application No. 61/081,337 filed on Jul. 16, 2008, the disclosure of which is incorporated herein by reference in its entirety. Volume of Reactor-1 was 5 ml and its dimensions were 5/16" ID×4" Long. True density of de-lignified corn stover was taken as 0.5 g/ml for residence time calculation.

TABLE 4

Reaction conditions and maximum TOC observed for de-lignified corn stover.

| Experiment ID | Initial mass of corn stover (mg) | Water inlet rate (g/min) | $CO_2$ inlet rate (g/min) | Residence time, (seconds) $\tau_1$ | $\tau_2$ | Maximum TOC observed (ppm) |
|---|---|---|---|---|---|---|
| E122107 | 1411.7 | 2 | 0.5 | 16 | 13.6 | 6731 |
| E122207 | 681.9 | 14 | 2 | 3.7 | 2.4 | 695.2 |

During experiment no. E122107, the pressure drop across the reactor was very high (about 1400 psi), so the water flow rate could not be increased more than 2 ml/min. Product came out as a dark brown solution in first 30 min of operation. After opening the Reactor-1, no solid residue was observed. The biomass was completely liquefied in first 30 min of operation.

In experiment E122207, TOC rise was observed in first 25 min of operation, and then it came down to 300 ppm level. After opening the Reactor-1, more than 50% of biomass was found to be unreacted. The solid residue was weighed after drying at 105° C. The reacted biomass was determined to be 279.76 mg (about 40% by weight of original mass). The liquid product was almost colorless and its volume was 260 ml. No dissolved solids were observed in the product.

Significant amount of cellulose came out as dissolved solids, when α-cellulose fibers were used for the experiments. After de-lignification, liquefaction of corn stover is observed to be faster and total organic compounds (TOC) starts rising just after 5 minutes. As the reaction proceeds, the void volume in the reactor changes continuously, changing the residence time in the semi-continuous experiments.

Example 2

Figure 2:
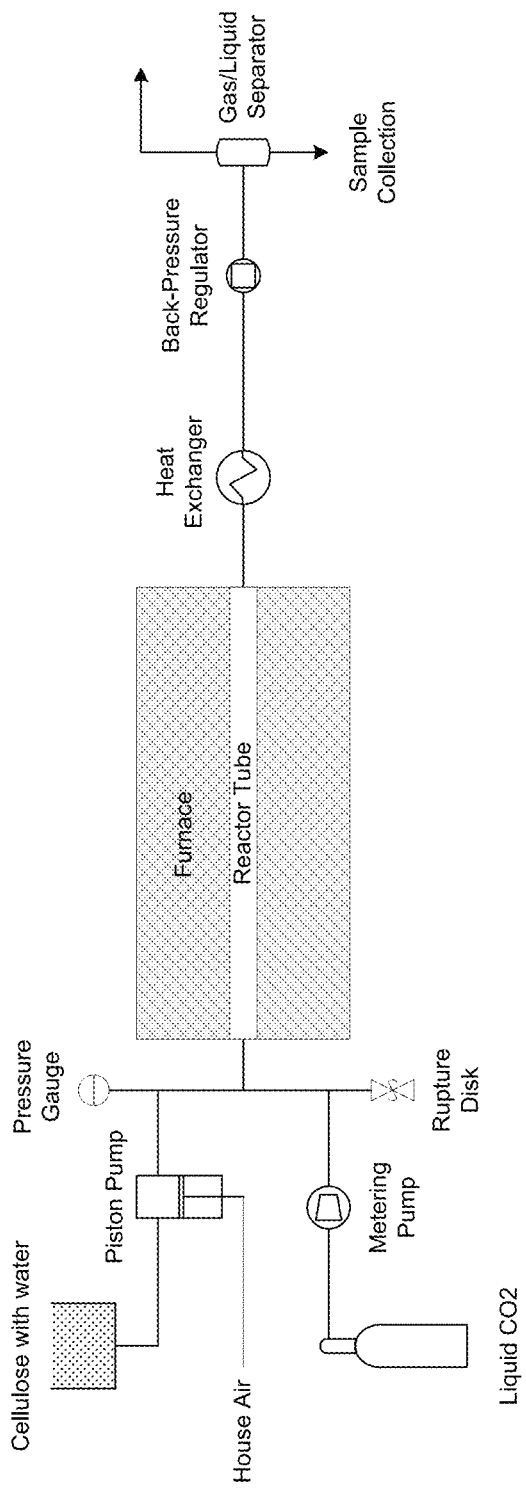
FIG. 2 depicts a schematic of an example of an apparatus used in a continuous cellulose hydrolysis process.

A Continuous Process for Cellulose Hydrolysis (a) A Continuous Process:

An apparatus for cellulose hydrolysis was designed and constructed (see schematic in FIG. 2). This apparatus both dissolved and hydrolyzed cellulose to produce sugars.

The process conditions were: 225 bar pressure, 10 mL reactor, and 300° C. for cellulose solubilization. The residence time (reaction time) is 10 seconds.

Typically, the reactor was placed inside the furnace, followed by the following steps: (i) Reactor and inlet line of $CO_2$ was heated to 300° C.; (ii) Cellulose slurry (4-5 wt % cellulose in water) was started at desired flow rate using piston pump; (iii) $CO_2$ flow was started at desired flow rate; (iv) Mixture was flowed through the reactor tube and then cooled to room temperature; (v) Liquid product samples were collected at desired intervals from the phase separator.

Figure 3:
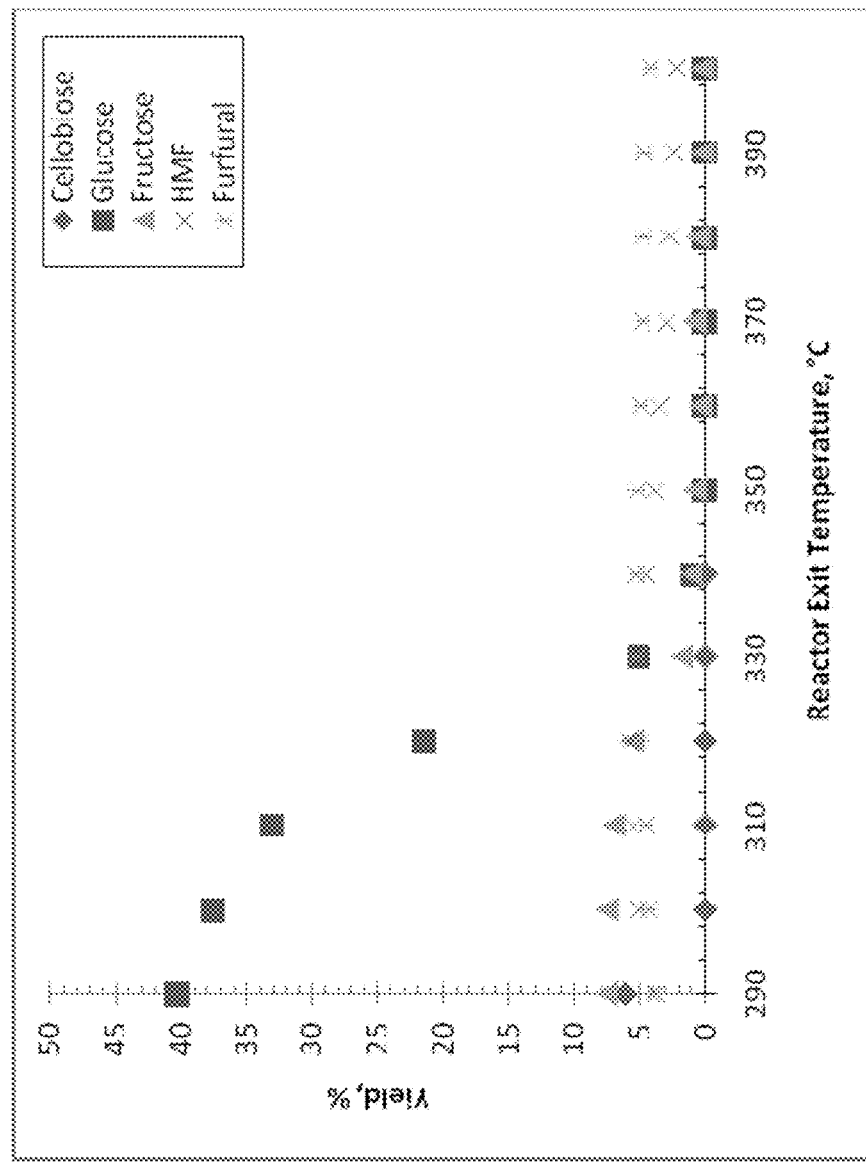
FIG. 3 is a graph of the yields from the continuous flow carbonic hydrothermal treatment of cellulose for different reactor exit temperatures; residence time is approximately 12 s.

The sugar analysis was done using HPLC using column Bio-Rad Aminex HPX-87P (Lead based column), RI detector, at 85° C., with water as the mobile phase. Known concentrations of glucose, fructose and cellobiose were injected in the column for calibration. The results suggest that $CO_2$ catalyzes the hydrolysis of cellulose without affecting the glucose decomposition reactions. FIG. 3 shows the percentage of yield of sugars for different reaction temperature.

Carbonic hydrothermal treatment of cellulose is a promising method for the production of glucose and fructose. The combination of supercritical $CO_2$ and water significantly improved the glucose yield at lower temperatures while the yields of other species remained about the same.

(b) Hydrolysis of Cellulose Derived from Woody Biomass:

Cellulose derived from woody biomass was used as substrate (containing 73% glucan) in a continuous cellulose hydrolysis process. This example involved hydrolyzing the cellulose using supercritical carbon dioxide and supercritical water at about 371-377° C. and about 225 bar for about 0.12-0.3 seconds (based on water density at process conditions). A slurry of cellulose in water was mixed with $CO_2$; the mixture was heated in a furnace to a pre-set temperature between 220° C. to 280° C. before fed to the reactor, which is heated using a heating jacket to about 371-377° C. At the end of the reaction time, the reaction was quenched and the products are analyzed. As the results below show, cellulose was solubilized and glucose monomers and oligomers were obtained. The glucose reported is the total of monomers and oligomers.

TABLE 5

Reaction conditions and maximum TOC observed for de-lignified corn stover.

| | Cellulose slurry temperature, ° C. | Final mixture temperature, ° C. | t, min | Mass solubilized, % | Glucose yield (incoming basis), % | Glucose yield (solubilized basis), % |
|---|---|---|---|---|---|---|
| 1 | 280 | 372   | 0.005 | 37.8 | 15   | 39.7 |
| 2 | 280 | 376.5 | 0.002 | 40.6 | 27   | 66.6 |
| 3 | 250 | 372.5 | 0.005 | 32.5 | 27.5 | 84.6 |
| 4 | 250 | 376.5 | 0.002 | 41   | 36.5 | 89.0 |
| 5 | 220 | 371   | 0.005 | 46   | 44   | 95.7 |
| 6 | 220 | 375   | 0.002 | 41   | 39   | 95.1 |

This shows successful demonstration of the first stage of cellulose hydrolysis. The un-solubilized cellulose can be processed further using a hydrolysis method described to improve yields.

Although the foregoing invention has been described in some detail by way of illustration and example for purposes of clarity of understanding, it will be apparent to those skilled in the art that certain changes and modifications may be practiced without departing from the invention. Therefore, the descriptions and examples should not be construed as limiting the scope of the invention.

It should be noted that, as used herein, the singular form "a", "an", and "the" includes plural references unless indicated otherwise. Additionally, as used herein, the term "comprising" and its cognates are used in their inclusive sense; that is, equivalent to the term "including" and its corresponding cognates.

All patents, patent applications, documents, and articles cited herein are incorporated by reference in their entireties.

What is claimed is:

1. A process for hydrolyzing cellulose, comprising:
    (a) contacting cellulose with a fluid mixture comprising supercritical $CO_2$ and sub-critical or near-critical water to form a reactant mixture at a first temperature and first pressure for a first time period, wherein a reaction occurs and forms one or more hydrolysis products;
    (b) quenching the reaction; and
    (c) recovering at least one hydrolysis product.

2. The process of claim 1, wherein the fluid mixture comprises about 5 wt % to about 20 wt % $CO_2$.

3. The process of claim 1, wherein the reaction is performed at a pH of about 3 to about 5.

4. The process of claim 1, wherein the first time period is about 1 s to about 30 s.

5. The process of claim 1, wherein the reaction is quenched by cooling the reactant mixture to a temperature of about 30° C. to about 80° C.

6. The process of claim 1, wherein prior to step (a), the cellulose is solubilized by
    (1) contacting the cellulose with near-critical or supercritical water at a second temperature and a second pressure for a second time period; and
    (2) quenching the solubilization reaction.

7. The process of claim 6, wherein the second temperature is about 373° C. to about 420° C.

8. The process of claim 6, wherein the second pressure is about 200 bar to about 350 bar.

9. The process of claim 6, wherein the second time period is about 0.1 s to about 5 s.

10. The process of claim 6, wherein the solubilization reaction is quenched by lowering the temperature to about 280° C.

11. The process of claim 6, wherein the solubilization reaction is quenched with $CO_2$ and optionally water.

12. The process of claim 1, wherein the at least one hydrolysis product is selected from the group consisting of glucose, fructose, mannose, cellobiose and oligomers thereof.

13. The process of claim 1, wherein the process is a continuous process, a semi-continuous process or a batch process.

14. The process of claim 1, wherein the first temperature is about 270° C. to about 320° C.

15. The process of claim 1, wherein the first pressure is about 180 bar to about 350 bar.

* * * * *